US010332253B2

United States Patent
Behar et al.

(10) Patent No.: US 10,332,253 B2
(45) Date of Patent: Jun. 25, 2019

(54) METHODS AND DEVICES FOR REGISTRATION OF IMAGE DATA SETS OF A TARGET REGION OF A PATIENT

(71) Applicants: Jonathan Behar, Barnet (GB); Alexander Brost, Erlangen (DE); Peter Mountney, London (GB); Maria Panayiotou, London (GB); Kawal Rhode, Croydon (GB); Aldo Rinaldi, London (GB); Daniel Toth, Twickenham (GB)

(72) Inventors: Jonathan Behar, Barnet (GB); Alexander Brost, Erlangen (DE); Peter Mountney, London (GB); Maria Panayiotou, London (GB); Kawal Rhode, Croydon (GB); Aldo Rinaldi, London (GB); Daniel Toth, Twickenham (GB)

( * ) Notice: Subject to any disclaimer, the term of this patent is extended or adjusted under 35 U.S.C. 154(b) by 1 day.

(21) Appl. No.: 15/633,858

(22) Filed: Jun. 27, 2017

(65) Prior Publication Data
US 2017/0372474 A1 Dec. 28, 2017

(30) Foreign Application Priority Data
Jun. 28, 2016 (EP) .................................... 16176653

(51) Int. Cl.
*G06T 7/00* (2017.01)
*A61B 5/00* (2006.01)
(Continued)

(52) U.S. Cl.
CPC .......... *G06T 7/0012* (2013.01); *A61B 5/0035* (2013.01); *A61B 6/037* (2013.01);
(Continued)

(58) Field of Classification Search
CPC .......... G06T 7/0012; G06T 7/11; G06T 7/344
(Continued)

(56) References Cited

U.S. PATENT DOCUMENTS

| 5,568,384 A | 10/1996 | Robb et al. |
| 2010/0036233 A1 | 2/2010 | Zhu et al. |

(Continued)

FOREIGN PATENT DOCUMENTS

| EP | 1912174 A2 | 4/2008 |
| WO | WO0145047 A1 | 6/2001 |
| WO | WO2009081318 A1 | 7/2009 |

OTHER PUBLICATIONS

Bourier F, et al.: "Coronary Sinus Extraction for Multimodality Registration to guide Transseptal Puncture", in: 8th Interventional MRI Symposium. pp. 311-313; 2010.
(Continued)

*Primary Examiner* — Justin P. Misleh
(74) *Attorney, Agent, or Firm* — Lempia Summerfield Katz LLC

(57) ABSTRACT

A method for registering image data sets of a target region of a patient includes selecting a first anatomical structure only or at least partially only visible in the first image data set, and a second anatomical structure only or at least partially only visible in the second image data set, such that there is a known geometrical relationship between extended segments of the anatomical structures; automatically determining a first geometry information describing the geometry of at least a part of the first anatomical structure and a second geometry information describing the geometry of at least a part of the second anatomical structure, neither information being sufficient to enable registration of the image data sets on its own; automatically optimizing transformation parameters describing a rigid transformation of one of the anatomical structures with respect to the other and geometrical
(Continued)

correspondences; and determining registration information from the optimized transformation parameters.

19 Claims, 2 Drawing Sheets

(51) Int. Cl.
    *A61B 6/03*         (2006.01)
    *A61B 17/00*       (2006.01)
    *A61B 90/00*       (2016.01)
    *G06T 7/33*         (2017.01)

(52) U.S. Cl.
    CPC .............. *A61B 2017/00243* (2013.01); *A61B 2090/364* (2016.02); *A61B 2090/367* (2016.02); *A61B 2090/374* (2016.02); *A61B 2090/376* (2016.02); *G06T 7/344* (2017.01); *G06T 2207/10088* (2013.01); *G06T 2207/10116* (2013.01); *G06T 2207/30004* (2013.01); *G06T 2207/30048* (2013.01); *G06T 2207/30101* (2013.01)

(58) Field of Classification Search
    USPC ....................................................... 382/128
    See application file for complete search history.

(56) References Cited

U.S. PATENT DOCUMENTS

| | | | |
|---|---|---|---|
| 2011/0069063 A1* | 3/2011 | Liao ..................... | A61B 6/5235 345/419 |
| 2012/0041318 A1* | 2/2012 | Taylor ................ | A61B 5/02007 600/504 |
| 2013/0094738 A1 | 4/2013 | Bond | |
| 2015/0042646 A1* | 2/2015 | Comaniciu ............. | G06T 17/20 345/420 |
| 2016/0171649 A1 | 6/2016 | Koo et al. | |

OTHER PUBLICATIONS

European Search Report for related European Application No. 16176653.0 dated Feb. 3, 2017.
Faber, T.L. et al.: "Three-Dimensional Fusion of Coronary Arteries with Myocardial Perfusion Distributions: Clinical Validation", in: Journal of Nuclear Medicine, vol. 45, No. 5, pp. 745-753, May 2004.
Hill; D. et al.: "Medical Image Registration Using Knowledge of Adjacency of Anatomical Structures", in: Image and Vision Computing 12 (3), pp. 439-448 (1994).
Hoffmann M., et al.: "Reconstruction method for curvilinear structures from two views", in: Medical Imaging, pp. 1-8; 2013.
Hoffmann, M. et al.: "Electrophysiology Catheter Detection and Reconstruction From Two Views in Fluoroscopic Images", in: IEEE Transactions on Medical Imaging, vol. 35, pp. 567-579 (2015).
Jolly M., et al.: "Automatic segmentation of the myocardium in cine MR images using deformable registration", in: STACOM Imaging and modelling intelligence, vol. 8896, pp. 1-10 (2011).
Kurzendorfer T., et al.: "Cryo-Balloon Catheter Localization Based on a Support-Vector-Machine Approach", in: IEEE Transactions on Medical Imaging, vol. 10, Nr. 10; pp. 1-11 (2016).
Myronenko Andriy et al..: "Point Set Registration: Coherent Point Drift"; Department of Science and Engineering, School of Medicine, Oregon Health and Science University Portland, OR, 97201, Mar. 18, 2010.
Panayiotou M., et al.: "A statistical method for retrospective cardiac and respiratory motion gating of interventional cardiac X-ray images", in: Med. Phys., vol. 41, Nr. 7, pp. 071901-1-071901-13, Jul. 2014.
Panayiotou M., et al.: "A statistical model of catheter motion from interventional x-ray images: application to image-based gating", in: Phys. Med. Biol., vol. 58, pp. 7543-7562; 2013.
Rhode, Kawal S. et al; "Registration and Tracking to Integrate X-Ray and MR Images in an XMR Facility"; in IEEE Transactions on Medical Imaging; vol. 22; No. 11; pp. 1369-1378; Nov. 2003.
Truong M., et al.: "Preliminary Investigation: 2D-3D Registration of MR and X-ray Cardiac Images Using Catheter Constraints", in: CI2BM09-MICCAI Workshop on Cardiovascular Interventional Imaging and Biophyiscal Modelling, 9 pages (2009).
Tsadok Y., et al.: "Automatic segmentation of cardiac MRI cines validated for long axis views", in: Computerized Medical Imaging and Graphics, vol. 37, pp. 500-511; 2013.
Yang J., et al.: "Go-ICP: A Globally Optimal Solution to 3D ICP Point-Set Registration", in: IEEE transactions on pattern analysis and machine intelligence, vol. 99, pp. 1-14; 2015.
Yang J., et al.: "Go-ICP: Solving 3D Registration Efficiently and Globally Optimally", in: IEEE International Conference on Computer Vision, pp. 1457- 1464; 2013.
Zhou, W. et al.: "3D Fusion of LV Venous Anatomy on Fluoroscopy Venograms With Epicardial Surface on SPECT Myocardial Perfusion Images for Guiding CRT LV Lead Placement", in: JACC Carciovascular Imaging, vol. 7, No. 12, 2014.

* cited by examiner

METHODS AND DEVICES FOR REGISTRATION OF IMAGE DATA SETS OF A TARGET REGION OF A PATIENT

The application claims the benefit of European Patent Application No. EP16176653, filed Jun. 28, 2016, which is hereby incorporated by reference in its entirety.

TECHNICAL FIELD

The disclosure relates to a method and a device for registration of a first image data set and a second image data set of a target region of a patient, wherein the first and the second image data set have been acquired using different imaging modalities or using different imaging techniques on the same imaging modality. Additionally, the disclosure relates a computer program and an electronically readable storage medium.

BACKGROUND

In medical applications, a target region of a patient may be imaged with two or more different modalities to obtain additional information that one single modality would not be able to depict. Spatially aligning complementary information from two or more image modalities has a wide range of applications including diagnostics, planning, simulation, and guidance. The registration of image data sets from different modalities has been extensively studied and many solutions have been proposed. Many of these approaches require at least some of the same anatomy or landmarks to be visible in both modalities. This cross-modality information is used to perform the registration. However, in many cases, there is little or no cross-modality information such that a registration cannot be based on it. Thus, known methods such as using landmarks, image intensity, mutual information, gradient based approaches, and learning similarity functions cannot be applied.

In image guided interventions, such as cardiac resynchronization therapy ("CRT"), pre-operative magnetic resonance (MR), or single-photon emission computed tomography (SPECT) images are used to analyze tissue characteristics or function and intraoperative X-ray fluoroscopy is used to guide the procedure. The pre- and intra-operative modalities are fundamentally different and do not share significant cross-modality information. In such cases, alternative registration strategies are required.

In a paper by K. S. Rhode et al, "Registration and tracking to integrate X-ray and MR images in an XMR facility", in IEEE TMI 22(11), pp. 1369-1378 (2003), it has been proposed to use fiducial markers and optical tracking devices for registration in cardiac resynchronization therapy. However, this approach requires pre-operative and MR imaging immediately before the procedure and additional hardware in the operating room. Additionally, anatomical registration has been proposed where the position of the vessels is inferred from catheters and aligned to vessels segmented from pre-operative images (see, e.g., Bourier et al., "Coronary Sinus Extraction for Multimodality Registration to Guide Transseptal Puncture," 8th Interventional MRI Symposium, pp. 311-313 (2010); and Truong et al., "Preliminary Investigation: 2D-3D Registration of MR and X-ray Cardiac Images Using Catheter Constraints," pp. 1-9 (2009)). However, catheters may deform the vessels and the resolution of magnetic resonance may be too low to accurately segment the vessels.

In the scope of planning and visualizing, Faber et al., "Three-Dimensional Fusion of Coronary Arteries with Myocardial Perfusion Distributions: Clinical Validation," J. Nucl. Med. 2004 (45), pp. 745-753, proposed to register a pre-operative SPECT image data set to fluoroscopy image data sets by manually matching landmarks, (e.g., interventricular grooves to coronary artery vessels), performing an iterative closest point (ICP) refinement, and finally do a non-linear warping to gain an image with fused information to visualize the left ventricle and its surroundings, in particular for planning purposes. This method is dependent on accurately identifying landmarks in pre-operative data that is challenging as variations of the anatomy may result in inaccuracies. Additionally, an accurate registration between a pre-operative first image data set and a second image data set is not achieved because of these inaccuracies and non-linear warping steps to improve the visualization. The method cannot be used for image guidance during an intervention anyway, because manual placement of blood vessels in the respective grooves has to be performed to enable ICP finding a suitable starting point.

SUMMARY AND DESCRIPTION

The scope of the present disclosure is defined solely by the appended claims and is not affected to any degree by the statements within this description. The present embodiments may obviate one or more of the drawbacks or limitations in the related art.

It is an object of the present disclosure to provide a novel approach for registering multi-modal images sharing not enough common information to base a registration thereon, which may be performed fully automatic and results in an accurate registration information that may also be used for image-based guidance during interventions.

This object is achieved by a method, a registration device, a computer program, and an electronically readable storage medium.

The method for registration of a first image data set and a second image data set of a target region of a patient, wherein the first and the second image data sets have been acquired using different imaging modalities, includes the following acts: (1) selecting a first anatomical structure only or at least partially only visible in the first image data set, and a second anatomical structure only or at least partially only visible in the second image data set, such that there is a known geometrical relationship between at least extended segments of the anatomical structures; (2) by evaluating the first and second image data sets, automatically determining a first geometry information describing the geometry of at least a part of the first anatomical structure including the respective segment and a second geometry information describing the geometry of at least a part of the second anatomical structure including the respective segment, neither information concerning the first anatomical structure nor information concerning the second anatomical structure being sufficient to enable registration of the image data sets on its own; (3) automatically optimizing transformation parameters describing a rigid transformation of one of the anatomical structures with respect to the other and geometrical correspondences between features in the first and second geometry information by minimizing deviations from the known geometrical relationship; and (4) determining registration information from the optimized transformation parameters.

In certain examples, the first anatomical structure is different from the second anatomical structure. In many cases, the first anatomical structure is only visible in the first image data set, while the second anatomical structure is only visible in the second image data set. In some examples, the anatomical structures may be at least partially visible in both image data sets, but the in particular automatically deducible information is not sufficient to facilitate the registration. In other words, neither information concerning the first anatomical structure nor information concerning the second anatomical structure determined by evaluating the image data sets is sufficient to enable registration of the image data sets on its own.

The disclosure exploits the fact that even if there are no anatomical structures visible in both image data sets to facilitate a registration, there may be anatomical structures whose geometrical relationship may be at least partly, that is, for extended segments, known. To facilitate a registration process, it is not sufficient to have a point correspondence or a known geometrical relationship for a single point, but the segments have to be extended, wherein areas, (e.g., surfaces), may be used as segments. If at least geometrical information describing the segments of the first and second anatomical structures, for which the geometrical relationship is known, may be calculated accurately enough from the two image data sets, the segments may be aligned according to the geometrical relationship in a suitable optimization process to yield transformation parameters describing the transformation between the two image data sets and thus, enabling the calculation of registration information to register the image data sets, and thus, also facilitate registration between images subsequently acquired using the image device of the second image data set as long as the patient does not move in a relevant manner.

The disclosure is also applicable to the registration of more than two image data sets and/or more than two modalities, (e.g., having multiple second image data sets or even a third image data sets), wherein geometrical relationships encompassing three anatomical structures are used. An application of the method also includes image acquired over time, (e.g., a 4D data set like CINE MRI), where a single first image data set and its first anatomical structure may be used for registration to all partial image data sets of a temporal sequence as second image data sets.

In this and the following, image data set and imaging modality may be broadly interpreted as also encompassing other methods to gather multidimensional information on the geometry of anatomical structures and the resulting multidimensional anatomical datasets describing these geometries. For example, these modalities may include electro-anatomical mapping methods and related methods. In these cases, it is possible that the image data sets already only contain the anatomical structures, simplifying segmentation, and/or that they already include point cloud representations and/or surface representations, (e.g., meshes). The image data set may already have been derived from at least one original image data set, for example, by using CAD (Computer Aided Diagnostics) and/or as a parametrized model.

Additionally, the described registration process is not only applicable to different modalities, but also to different imaging techniques using the same modality. For example, the first image data set may be a contrast-enhanced x-ray image data set, (e.g., a digital subtraction angiography (DSA) image data set), and the second image data set may be a non-contrast-enhanced image data set.

As the registration process is fully automatic and may be realized in real-time, no manual interaction is required and the registration information may be used advantageously for image guidance in medical interventions in the target region of the patient. As only the geometry of the segments and the known geometrical relationship has to be known, the method has a broad spectrum of applications and may also be used for magnetic resonance image data sets that may have a lower spatial resolution such that for example the geometry of extended areas or surfaces may be deduced, but finer structures, such as grooves, wherein other anatomical structures lie, cannot be seen.

In an advantageous embodiment, the known geometrical relationship describes at least partly parallel or touching or intersecting surfaces of the anatomical structures. In particular, adjacent anatomical structures are used, which share at least partly parallel, intersecting or touching surfaces as extended segments, for which the geometrical relationship is known. The core of the proposed registration approach in this embodiment is the use of anatomical structures that are adjacent or share a common surface.

The first anatomical structure may be a tissue layer delimiting an organ and/or organ part, or adjacent to a secondary tissue layer delimiting an organ and/or organ part, in particular the myocardium or the epicardium, and the second anatomical structure is a blood vessel structure and/or parallel to the surface of the organ. Parallel in this case may be understood as at least following the curvature of the surface. In particular, the first anatomical structure may, in cardiac anatomy, be the epicardial surface of the left ventricle (LV), which is adjacent to the coronary sinus (CS) blood vessel tree as a second anatomical structure. The left ventricle is visible in the operative magnetic resonance image data sets, but the coronary sinus blood vessel tree is not. The blood vessel tree is visible during contrast enhanced x-ray fluoroscopy, however, the left ventricle is not. Because it is known that the coronary sinus blood vessel tree extends parallel or on the epicardial surface of the left ventricle, this prior anatomical knowledge, the known geometrical relationship, may be exploited to register multi-modal images without cross-modality image information.

While the cardiac anatomy, (e.g., the left ventricle), is used to explain concepts of the disclosure, the method described is also applicable in other areas of the human body, e.g., for different anatomical structures. For example, for organs such as the liver or the kidneys, it is known that blood vessel structures are found on the surface of these organs. This also holds to for certain kinds of tumors. Another area of application for the described method is the brain anatomy, where, for example, gray matter is adjacent to the meninx (cerebral membrane) and its blood vessels. Other examples include registering the spine (e.g., holes in vertebrae) to the spinal cord or to nerves extending through the spinal cord, and registration of the liver to the diaphragm.

In certain examples, the first image data set may be a magnetic resonance image data set and the second image data set may be an x-ray image data set. The x-ray image data set may be a fluoroscopy image data set, e.g., a biplane fluoroscopy image data set or a rotational angiographic x-ray image data set recorded during or at the onset of an intervention, as will be further discussed below in detail. For example, a biplane x-ray device having c-arms may be used.

The first geometry information may be determined using tissue segmentation. For example, for magnetic resonance image data sets, multiple algorithms have been proposed to segment certain types of tissue, (e.g., myocardial tissue). In an embodiment, the epicardial contour may be detected in a magnetic resonance data set using a combination of machine learning landmark detection and gray level analysis, as for example described in an article by M. P. Jolly et al., "Automatic segmentation of the myocardium in cine MR images using deformable registration," STACOM—Imaging and modelling intelligence, Vol. 8896, pp. 105-113 (2011). A mesh may then be fit to contours to generate a surface representation of the left ventricle epicardium at end diastole. For other areas of application, (e.g., brain anatomy), similar algorithms are known and have been proposed.

The second geometry information may be determined using vessel segmentation on the second image data set, which may be acquired using a contrast agent. The imaging of blood vessels may be performed using x-ray techniques. While in rotational angiography x-ray image data sets corresponding pixels showing the same blood vessel are easier to detect, it is also possible to achieve automatic determination of the geometry information for two x-ray projections imaged in two different planes, e.g., biplane fluoroscopy image data sets.

Thus, in an embodiment, when reconstructing a blood vessel structure as second anatomical structure from multiple two dimensional x-ray images of the second image data set, at least one specific point identifiable in each of the x-ray images, (e.g., at least one specific point of a medical instrument used to temporarily block a blood vessel and/or a specific point of a vessel bifurcation), is detected in all x-ray images and, using the specific point as a starting point, pixels corresponding to the same blood vessel are detected using the constraint that the blood vessel tree is interconnected. While in the past, it has been difficult to reconstruct a blood vessel tree automatically from a few two dimensional fluoroscopy images, such that in many cases manual interaction was required to find corresponding blood vessels in all projections, recently techniques have been proposed that allow automatic segmentation of blood vessel trees also in sparse sets of projections, using specific points that may be detected in all two dimensional images of the image data set as a starting point and exploiting the fact that the blood vessels are all interconnected. In this manner, even if, in particular in image guidance situations during interventions, only a few different projections are available as two-dimensional x-ray images, (e.g., two two-dimensional images in biplane fluoroscopy), a completely automatic registration process including the segmentation of the anatomical structures may be achieved in a reliable way.

The specific point may be a feature point of a medical instrument, (e.g., a catheter). In CRT, balloon catheters may be used to supply contrast agent and/or prevent reflux of the contrast agent from the vessels to be contrasted. Such a medical instrument may be automatically detected in all projections of a fluoroscopy image data set and thus supply a specific point from where to start the reconstruction of the vessel tree. For example, the detection of catheters in biplane fluoroscopy has been described in an article by Hoffmann et al., "Electrophysiology Catheter Detection and Reconstruction from Two Views in Fluoroscopic Images," IEEE Transactions on Medical Imaging, Vol. 35, pp. 567-579 (2015). It has also been proposed to localize a balloon catheter based on a support-vector-machine approach by Kurzendorfer et al., "Cryo-Balloon Catheter Localization Based on a Support-Vector-Machine Approach," IEEE Transactions on Medical Imaging, DOI: 10.1109/TMI.2016.2537052.

Methods as these may also be applied to localize specific points for the reconstruction of a blood vessel tree. Alternatively, or additionally, specific points of automatically detectable and identifiable bifurcations may be used. Regarding the reconstruction of the blood vessel tree starting at a specific point in the blood vessel tree, reconstruction methods for curvilinear structures from two views have also been discussed, (see, e.g., Hoffmann et al., "Reconstruction method for curvilinear structures from two Views," Medical Imaging 2013: Image-Guided Procedures, Robotic Interventions, and Modeling, edited by David R. Holmes and Ziv R. Yaniv, Proc. of SPIE Vol. 8671, 86712F (2013)), and may also be applied to the reconstruction of blood vessel trees, taking into account the boundary condition that the blood vessels are interconnected.

In one example, the first and/or second geometry information include a point cloud representation and/or a surface representation, (e.g., a mesh). Such representations of the segments, for which a known geometrical relationship exists, may with special advantage be used when adjacent parallel surfaces are evaluated. In particular, the method may perform point-to-point-registration or point-to-plane registration, registering point clouds with each other or point clouds with a surface.

Many algorithms registering point cloud representations or surface representations as such require carefully chosen initial sets of parameters because they may only detect local minima of the error functions or deviation functions. The current disclosure exploits the fact that that recently so-called globally optimized (Go) algorithms have been proposed that allow finding global minima of such registration problems by combining these algorithms with global search algorithms.

Thus, in one example, a globally optimized registration algorithm is used for optimizing the transformation parameters, e.g., a globally optimized iterative closest point algorithm (Go-ICP). While an ICP-algorithm may be used, other algorithms may also be used, such as Coherent Point Drift algorithms (CPD), as described, for example, by Andriy Myronenko and Xubo Song in "Point Set Registration: Coherent Point Drift," IEEE Transactions on Pattern Analysis and Machine Intelligence, vol. 32, pp. 2262-2275 (2010). In an article by J. Yang et al., "Solving 3D Registration Efficiently and Globally Optimally," in: 2013 IEEE ICCV, pp. 1457-1464 (2013), a branch and bound (BnB) algorithm is combined with an ICP algorithm to overcome their individual weaknesses, thus to provide a fast globally optimal solution. This Go-ICP algorithm guarantees convergence to the globally optimal solution. It is additionally much more efficient than the standard BnB algorithm, because even if it explores the whole possible solution space, it refines the intermediate results with the ICP method, thus benefiting from the good attributes of both algorithms.

For example, if a reconstructed blood vessel structure, is used wherein the geometry information is a point cloud representation, the registration problem may be described as a partial point cloud matching problem with unknown point correspondences. The rigid transformation may be described as a rotation and a translation, however, also the correspondences of features, for example points to vertices has to be taken into account. If the optimal rotation and translation was known, the correspondences may be found easily and if the correspondences were known, the optimal rotation and transformation would be easy to calculate. This problem of unknowns is solved by the ICP algorithm, which finds the nearest local minimum, however, additionally using the BnB algorithm as proposed by J. Yang et al. in their Go-ICP algorithm yields the globally optimal solution in a fast and reliable manner.

It is noted that, if one of the anatomical structures is a blood vessel structure extending on a surface of the other anatomical structure, the blood vessel structure may be evaluated regarding the surfaces of the blood vessels oriented in the direction of the surface such that a point cloud may be reduced for registration purposes.

In one embodiment, a boundary condition describing possible motion of the patient between acquisitions of the first and the second image data set is used to reduce the parameter space of the optimization of the transformation parameters. In particular, the boundary condition may be determined considering known positioning information of the patient during acquisition of the first and second image data set. In this manner, information about the positioning of the patient may be used to reduce the parameter space to be searched in the course of the registration. For example, if the patient has been imaged in both cases in the supine position, transformations assuming a turning of the patient to a prone position may be excluded.

At least one correlation information regarding the first and the second image data set, which is relevant regarding the registration, but not sufficient for registering the image data sets, may be used as a part of an optimization target function and/or as a boundary condition while optimizing the transformation parameters and/or for refining the registration information. In particular, the correlation information may include a point correspondence or a line correspondence. Even in cases in which extended anatomical structures cannot be fully visible in the image data sets of both modalities, there may be some mutual information, which alone is not sufficient to register the image data sets, but may be used to increase the accuracy of the registration, check the plausibility of the registration and/or enable a faster computing process. The method is improved by involving information that is common in the two modalities. For example, in cardiac registration, some parts of the vascular tree may even be identified in a magnetic resonance image data set. In another example, the shadow of the heart border, (e.g., the border of the left ventricle), may be identifiable in interventional fluoroscopy images of an X-ray image data set. Thus, in a concrete embodiment, the registration information may be refined by an adaptation to such features identifiable in an interventional image, (e.g., the shadow of the left ventricle).

Some target regions of patients may also be subjected to motion during acquisition of at least one of the image data sets. When parts of at least one of the image data sets are acquired in different motion states of a patient motion, in particular, an at least partly periodical motion, a motion state of at least one part of the image data set may be selected and parts acquired during other motion states may be transformed to the selected motion state. While, in a cardiac application, the images are commonly acquired during a breath hold state of the patient, the periodical heart motion still has an influence on parts of the image data set. If an image data set includes parts acquired in different motion states, the motion may be extracted such that all parts of the image data set may be converted to a certain, predetermined, selected motion state. In particular, a motion model, (e.g., based on a primary component analysis of the motion), may be used to describe the motion states and transformations between motion states. An approach using masked principle component analysis motion gating is described by M. Panayiotou et al. in "A statistical method for retrospective cardiac and respiratory motion gating of interventional cardiac X-ray images," Medical Physics 41(7), 071901 (2014).

As already mentioned, an advantageous area of application of the fully automatic registration of multi-modal image data sets is during image-guided interventions. Thus, the registration information may be used in calculating a fusion image for image guidance during a medical interventional procedure, (e.g., in a method for image guidance during an interventional medical procedure in the target region), wherein the registration information is used in generating a displayed fusion image incorporating information from both image data sets, or, for example, if the modality of the second image data set is the interventional modality, incorporating information from or associated with the first image data set and information from subsequent images of the imaging device of the second image data set, at least as long as the patient did not or only irrelevantly move. Commonly, the first image data set, (e.g., a magnetic resonance image data set), will be a pre-operative image data set already used for planning of the interventional procedure. The second image data set in such a case includes interventional images, (e.g., fluoroscopy images), which may depict the used medical instruments, for example, in a blood vessel structure in the target region of the patient. It is thus advantageous to calculate a fusion image by using at least a part of each image data set and/or subsequent images of the imaging device of the second image data set using the registration information. Parts of a pre-operative image data set may be overlaid onto interventional images of the interventional modality. Fusion images may also include information deducted from the image data sets, for example, results of a planning stage preceding the interventional procedure. Markers and/or additional information relating to the first image data set may be overlaid onto image data from the second image data set or subsequent images, which, for example, are no longer contrast enhanced. In this manner, accurate guidance during a medical interventional procedure is achieved.

In this context, it is also possible when during an interventional procedure in the target region the second image data set is reacquired at least once and with each reacquisition of the second image data set the registration information is updated, in particular, based on the previously determined registration information and/or in real time. As the registration process is running fully automatically, it is possible to update the registration information in real time, for example, by re-running the registration process using the most recently acquired interventional image data also showing the second anatomical structure. In case the second image data set includes contrast enhanced image date, a contrast enhanced reacquisition may be initiated if the registration information is to be updated, while the image guidance used subsequent non-contrast-enhanced images of the second modality. For example, if a patient motion is observed, a new contrast-enhanced acquisition may be triggered automatically or initiated by a user. Alternatively, the above-mentioned sparse common information between the modalities may also be used to update the registration information by refining using this cross-modality information, which may not suffice for registering image data sets, but for updating an already known registration information, in particular, from non-contrast-enhanced images of the second modality. It is noted that when using algorithms like Go-ICP, using the previously calculated registration information as a starting point may not be necessary because the whole parameter space (if not reduced as in embodiments described above) is searched.

In another aspect, the disclosure also includes a registration device for registration of a first image data set and a second image data set of a target region of a patient, wherein the first and the second image data sets have been acquired using different imaging modalities or using different imaging techniques on the same imaging modality. The registration device includes: (1) a selection unit for selecting a first anatomical structure only or at least partially only visible in the first image data set, and a second anatomical structure only or at least partially only visible in the second image data set, such that there is a known geometrical relationship between at least extended segments of the anatomical structures; (2) an evaluation unit for automatically determining, by evaluating the first and second image data sets, a first geometry information describing the geometry of at least a part of the first anatomical structure including the respective segment and a second geometry information describing the geometry of at least a part of the second anatomical structure including the respective segment, neither information concerning the first anatomical structure nor information concerning the second anatomical structure being sufficient to enable registration of the image data sets on its own; (3) an optimization unit for automatically optimizing transformation parameters describing a rigid transformation of one of the anatomical structures with respect to the other and geometrical correspondences between features of the first and second geometry information by minimizing deviations from the known geometrical relationship; and (4) a registration unit for determining registration information from the optimized transformation parameters.

In other words, the registration device is configured to perform the method. Consequently, all remarks and features concerning the method are also applicable to the registration device. The registration device may include a computer and/or at least one processor, wherein the units described may be implemented as hardware components and/or software components.

In a further aspect, the disclosure relates to a computer program that executes the acts of a method when the computer program is executed on a computer. The computer program may be stored on an electronically readable storage medium, on which a computer program is stored. The electronically readable storage medium may be a non-transitory storage medium, for example a CD.

In summary, the described embodiments reduce the difficulty of the registration process significantly, e.g., by omitting manual acts. The registration process becomes a "one click" process. The registration time is reduced with a potential of increased accuracy. The proposed registration process is able to register multi-modal images that do not share cross modality information/landmarks and is able to automatically update the registration in case of patient movement. The registration process is fully automated and finds the optimal solution of the registration problem. It is particularly advantageous for CRT interventions and may open up a new way of intermodality registration for multiple other fields of application.

BRIEF DESCRIPTION OF THE DRAWINGS

Further advantages and details of the current disclosure are apparent from the following description of the embodiments in conjunction with the drawings, in which.

DETAILED DESCRIPTION

Figure 1:
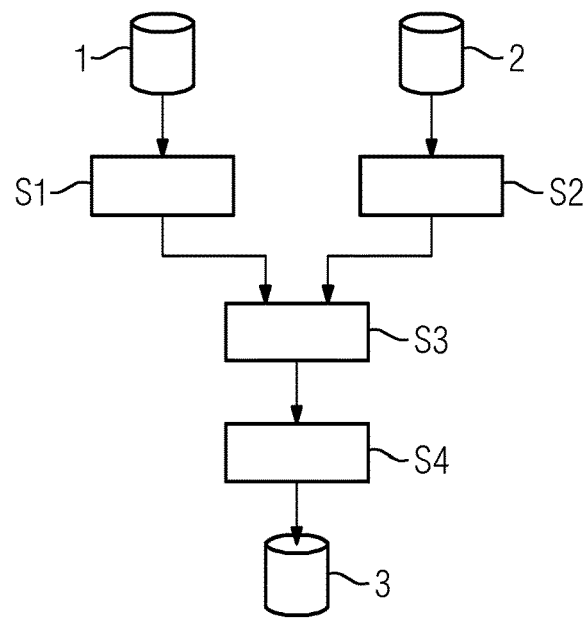
FIG. 1 depicts a flow chart of an embodiment of the method.

FIG. 1 is a flow chart of an embodiment of a method, which is used for image guidance during a medical interventional procedure, e.g., a CRT procedure. Pre-operatively, a magnetic resonance image data set has been acquired as a first image data set. Additionally, to the mentioned anatomical magnetic resonance image data set, a functional magnetic resonance image data set has been acquired to locate lesions in the left ventricle. The anatomical image data set has been used along with the functional magnetic resonance image data set to plan the intervention, e.g., to locate lesions and intervention locations on the epicardial surface of the myocardium.

During the actual intervention, a minimally invasive medical instrument, (e.g., a catheter), is used. To be able to guide the intervention, a biplane angiographic imaging device is used to acquire fluoroscopic images in different angulations showing the target region of the patient, such as the coronary sinus blood vessel tree due to application of a contrast agent. Two dimensional fluoroscopic images are also used to show the medical instrument. All these images form a second image data set.

The pre- and intra-operative modalities are fundamentally different such that the first image data set and at the second image data set do not share significant cross-modality information. However, for image guidance during the interventional procedure, a registration is needed to be able to accurately overlay information from the pre-operative first magnetic resonance image data set and/or planning information derived from the pre-operative imaging onto the fluoroscopic images of the second x-ray image data set showing the medical instrument and the blood vessel tree. To calculate registration information, the first image data set 1 and the second image data 2 are used as input data. To facilitate registration, two anatomical structures have already been selected, wherein the first anatomical structure is only visible in the first image data set and the second anatomical structure is only visible in the second image data set. However, at least segments of these anatomical structures have a known geometrical relationship. In the cardiac application discussed here, the magnetic resonance image data set shows the myocardium of the left ventricle as a first anatomical structure, so that the epicardial surface of the myocardium may be derived on which may lie the coronary sinus blood vessel tree as the second anatomical structure visible in the second image data set 2. In other words, the first and the second anatomical structures are adjacent in the sense that they share a common surface or at least parallel surfaces.

In act S1, the myocardium is segmented in the first image data set 1 by using a known tissue segmentation algorithm not discussed here in detail. From the segmented myocardium, the epicardial surface may be derived and is described in act S1 as a surface representation, namely a mesh. The mesh may also be understood as a point cloud representation if the nodes are taken as single points; however, other possibilities exist to describe the epicardial surface as a point cloud representation alternatively or additionally. The surface representation and/or the point cloud representation constitutes a first geometry information.

In act S2, which is independent from act S1, the second image data set 2 is evaluated to derive a second geometry information describing the coronary sinus blood vessel tree as a point cloud representation. To achieve this, the two-dimensional fluoroscopy images of the second image data set are first analyzed to detect specific points visible in all two-dimensional fluoroscopy images. In this embodiment, the specific point is a feature point of the medical instrument; however, alternatively, or additionally, a specific point of an identifiable bifurcation in the blood vessel tree may be used. Knowing the location of the specific point in all two-dimensional projections of the second image data set 2, the blood vessel tree may be reconstructed, wherein the fact that the blood vessels are interconnected is used to assign pixels from the fluoroscopy images to certain blood vessels and find pixels showing the same blood vessel. To create a point cloud representation of the blood vessel tree, points along the center lines of the blood vessels may be used, and it is possible to use points on the circumference of the vessels, such as those on the surface oriented to the epicardial surface.

Once the first and the second geometry information are known, in act S3 registration is performed. In this embodiment, a Go-ICP algorithm is used to find the global optimum regarding the known relationship, e.g., minimizing the deviations from the known geometrical deviationship, for transformation parameters including those of a rigid transformation (e.g., rotation and translation) and feature correspondences, in the case of two point cloud representations point correspondences. Other algorithms, (e.g., a Go-CPD algorithm), may also be used. By using a globally optimized registration algorithm, a manual act wherein a first rough positioning is chosen as a starting point for finding a local minimum, may be omitted.

The Go-ICP algorithm may use boundary conditions reducing the parameter space to be searched. For example, positioning information from the acquisition of the first image data set 1 and the second image data set 2 may be used to exclude certain motions of the patient between the acquisitions. Additionally, sparse mutual information from the image data sets 1, 2, which is not sufficient to register them on its own, may be used to formulate boundary conditions.

It is, however, as indicated in FIG. 1, possible to use such information that is common in the two modalities in act S4 to refine the registration information calculated in act S3. For example, some parts of the vascular tree in the first magnetic resonance image data set 1 may be identified and/or the shadow of the border of the left ventricle or other components of the human heart may be extracted from fluoroscopy images of the second x-ray image data set 2.

The result of the method is accurate registration information 3 that may be used to create fusion images for image guidance, as will be detailed below.

Figure 2:
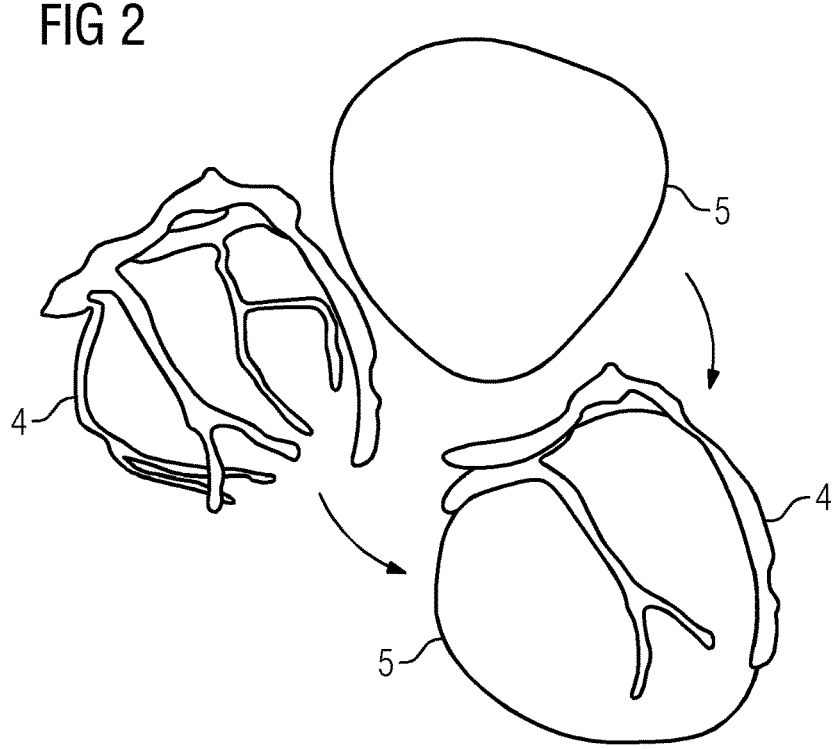
FIG. 2 depicts an example of a diagram visualizing a registration process.

FIG. 2 shows geometrically how the registration process works. The blood vessel tree 4 extracted from the second image data set 2 and the epicardial surface 5 of the myocardium as segmented from the first image data set 1 are positioned such that the blood vessel tree 4 optimally lies on the epicardial surface 5 of the myocardium.

It is noted that the registration information 3 may be updated automatically every time a new second image data set 2 is acquired during the interventional procedure, for example, if patient motion occurred and/or if requested by a user, who, for example, observed a patient motion, and/or periodically. In both cases, the registration process may be performed in real-time.

Figure 3:
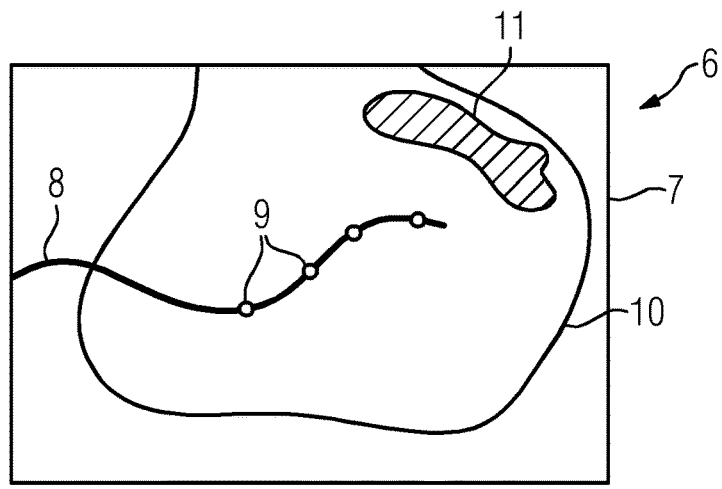
FIG. 3 depicts an example of a fusion image for image guidance.

The registration information 3 is used to create fusion images for image guidance during the interventional procedure. An example for such a fusion image is shown in FIG. 3. The fusion image 6 includes a fluoroscopy image 7 of the second image data set 2 or a fluoroscopy image acquired using the same imaging device as used for the second image data set 2 with no relevant patient motion occurring because acquisition of the second image data set 2, overlaid with information from the first image data set 1 and/or planning information from planning performed on the first image data set 1. The fluoroscopy image 7 shows a medical instrument 8, here a multipolar lead with electrodes 9. As an overlay, the epicardial surface 10 is included as well as areas containing lesions (e.g., scarred tissue), an information taken from the above-mentioned functional magnetic resonance image data set, which is registered with the anatomical magnetic resonance image data set forming the first image data set 1. Lesions, (e.g., scarred tissue), are shown as colored areas 11. As depicted, the electrodes 9 are placed to avoid scarred tissue.

Figure 4:
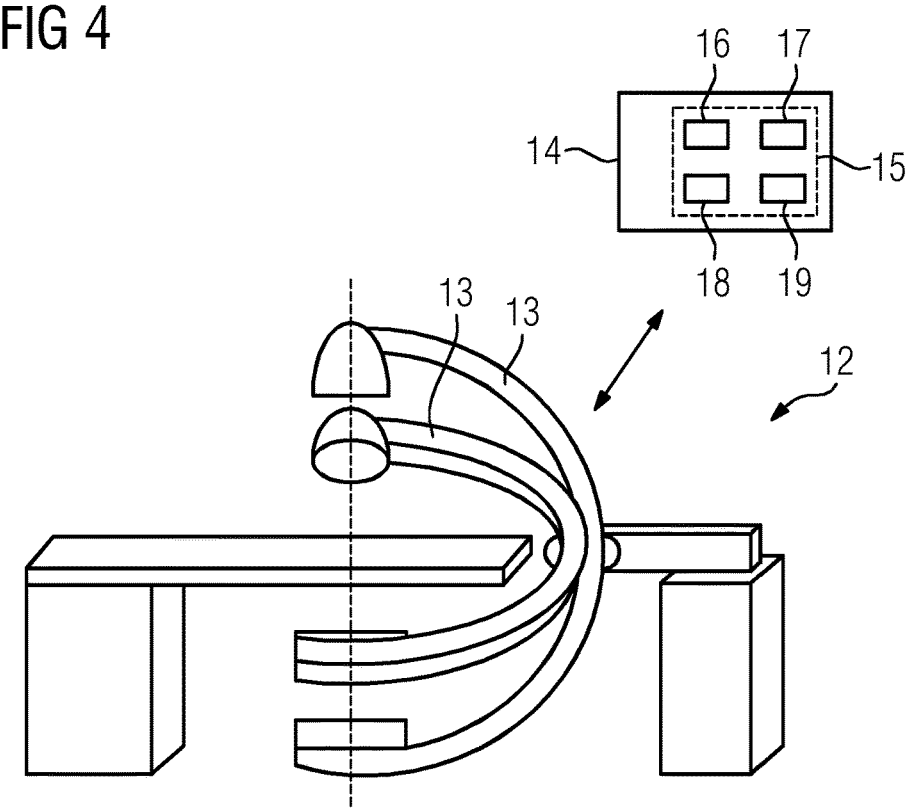
FIG. 4 depicts an example of an angiographic imaging device having an integrated registration device.

Finally, FIG. 4 shows an angiographic imaging device 12 having two C-arms 13 such that fluoroscopic images using two different angulations may be acquired simultaneously. The angiographic imaging device 12 has a control device 14, which, in this embodiment, also includes a registration device 15 configured to perform the method.

The registration device 15 includes a selection unit 16 for selecting the anatomical structures. For example, for multiple possible interventional procedures and combinations of modalities, suitable anatomical structures, and respective algorithms may be stored in a data base of the control unit 14.

The registration device 15 further includes an evaluation unit 17 for automatically determining the first and second geometry information and an optimization unit 18 for registering a geometry information. Finally, a registration unit 19 for determining the registration information from the optimized transformation parameters determined by the optimization unit 18 is provided.

Additionally, the control device 14 may also include a fusion unit using the registration information to generate fusion images such as a fusion image 6 shown in FIG. 3.

It is to be understood that the elements and features recited in the appended claims may be combined in different ways to produce new claims that likewise fall within the scope of the present disclosure. Thus, whereas the dependent claims appended below depend from only a single independent or dependent claim, it is to be understood that these dependent claims may, alternatively, be made to depend in the alternative from any preceding or following claim, whether independent or dependent, and that such new combinations are to be understood as forming a part of the present specification.

While the present disclosure has been described above by reference to various embodiments, it may be understood that many changes and modifications may be made to the described embodiments. It is therefore intended that the foregoing description be regarded as illustrative rather than limiting, and that it be understood that all equivalents and/or combinations of embodiments are intended to be included in this description.

The invention claimed is:

1. A method for registering a first image data set and a second image data set of a target region of a patient, the method comprising:

selecting a first anatomical structure only or at least partially only visible in the first image data set and a second anatomical structure only or at least partially only visible in the second image data set, wherein the first anatomical structure is different from the second anatomical structure, wherein the selection is based on a known geometrical relationship between the first and second anatomical structures, and wherein the first and the second image data sets have been acquired using different imaging modalities or using different imaging techniques on a same imaging modality;

automatically evaluating, by a processor, the first and second image data sets to determine first geometry information describing a geometry of at least a part of the first anatomical structure and second geometry information describing a geometry of at least a part of the second anatomical structure, wherein neither the first geometry information nor the second geometry information is independently able to register the first and second image data sets;

automatically optimizing, by the processor, transformation parameters by minimizing deviations from the known geometrical relationship, wherein the transformation parameters comprise a rigid transformation of one of the first or second anatomical structures with respect to the other anatomical structure and geometrical correspondences between features in the first and second geometry information;

determining registration information from the optimized transformation parameters;

registering the first image data set and the second image data set using the registration information to provide a fusion image; and displaying the fusion image.

2. The method of claim 1, wherein the known geometrical relationship describes as least partly parallel or touching or intersecting surfaces of the first and second anatomical structures.

3. The method of claim 1, wherein the first anatomical structure is a tissue layer delimiting an organ or organ part, or adjacent to a secondary tissue layer delimiting an organ or organ part, and
wherein the second anatomical structure is a blood vessel structure on or parallel to a surface of the organ.

4. The method of claim 3, wherein the first anatomical structure is an epicardium or a myocardium.

5. The method of claim 3, wherein the first geometry information is determined using tissue segmentation, or
wherein the second geometry information is determined using vessel segmentation.

6. The method of claim 1, wherein the first image data set has been acquired without a contrast agent, and
wherein the second image data set has been acquired using a contrast agent.

7. The method of claim 1, wherein the first image data set is a magnetic resonance image data set and the second image data set is an x-ray image data set.

8. The method of claim 7, wherein a blood vessel structure is reconstructed as the second anatomical structure from multiple two-dimensional x-ray images of the second image data set,
wherein a specific point identifiable in each of the x-ray images is detected in all x-ray images, and
wherein, using the specific point as a starting point, pixels corresponding to a same blood vessel are detected using a constraint that a blood vessel tree is interconnected.

9. The method of claim 8, wherein the specific point is a specific point of a medical instrument used to temporally block a blood vessel or a specific point of a bifurcation.

10. The method of claim 1, wherein the first geometry information, the second geometry information, or both the first and second geometry information comprise a point cloud representation, a surface representation, or both the point cloud representation and the surface representation.

11. The method of claim 10, wherein the surface representation is a mesh.

12. The method of claim 1, wherein a globally optimized iterative closest point algorithm, a globally optimized coherent point drift algorithm, or both the globally optimized iterative closest point algorithm and the globally optimized coherent point drift algorithm are used for optimizing the transformation parameters.

13. The method of claim 1, wherein a boundary condition describing possible motion of the patient between acquisition of the first image data set and the second image data set is used to reduce a parameter space of the optimization of the transformation parameters.

14. The method of claim 1, wherein at least one correlation information regarding the first image data set and the second image data set is used as a part of an optimization target function or as a boundary condition while optimizing the transformation parameters or for refining the registration information.

15. The method of claim 1, wherein the fusion image is created for image guidance during a medical interventional procedure.

16. The method of claim 1, further comprising:
reacquiring the second image data set at least once during an intervention in the target region; and updating the registration information with at least one reacquisition of the second image data set.

17. The method of claim 16, wherein the registration information is updated in real time.

18. A registration device for registration of a first image data set and a second image data set of a target region of a patient, wherein the first and the second image data sets have been acquired using different imaging modalities or using different imaging techniques on a same imaging modality, the registration device comprising:
a processor configured to:
select a first anatomical structure only or at least partially only visible in the first image data set and a second anatomical structure only or at least partially only visible in the second image data set, wherein the first anatomical structure is different from the second anatomical structure, and wherein the selection is based on a known geometrical relationship between the first and second anatomical structures;
automatically evaluate the first and second image data sets to determine first geometry information describing a geometry of at least a part of the first anatomical structure and second geometry information describing a geometry of at least a part of the second anatomical structure, wherein neither the first geometry information nor the second geometry information is independently able to register the first and second image data sets;
automatically optimize transformation parameters by minimizing deviations from the known geometrical relationship, wherein the transformation parameters comprise a rigid transformation of one of the first or second anatomical structures with respect to the other anatomical structure and geometrical correspondences between features in the first and second geometry information;
determine registration information from the optimized transformation parameters;

register the first image data set and the second image data set using the registration information to provide a fusion image; and display the fusion image.

19. A computer comprising:

a non-transitory electronically readable storage medium including a computer program that when executed, the non-transitory electronically readable storage medium and computer program configured to cause a computer to perform:

select a first anatomical structure only or at least partially only visible in a first image data set and a second anatomical structure only or at least partially only visible in a second image data set, wherein the first anatomical structure is different from the second anatomical structure, and wherein the selection is based on a known geometrical relationship between at least extended segments of the first and second anatomical structures;

automatically evaluate the first and second image data sets to determine first geometry information describing a geometry of at least a part of the first anatomical structure and second geometry information describing a geometry of at least a part of the second anatomical structure, wherein neither the first geometry information nor the second geometry information is independently able to register the first and second image data sets;

automatically optimize transformation parameters by minimizing deviations from the known geometrical relationship, wherein the transformation parameters comprise a rigid transformation of one of the first or second anatomical structures with respect to the other anatomical structure and geometrical correspondences between features in the first and second geometry information;

determine registration information from the optimized transformation parameters;

register the first image data set and the second image data set using the registration information to provide a fusion image; and display the fusion image.

* * * * *